(12) United States Patent
Auffray et al.

(10) Patent No.: US 10,429,354 B2
(45) Date of Patent: Oct. 1, 2019

(54) RECONFIGURABLE DEVICE FOR CHECKING A COMPOSITE STRUCTURE USING ULTRASOUND

(71) Applicant: EUROPEAN AERONAUTIC DEFENCE AND SPACE COMPANY EADS FRANCE, Paris (FR)

(72) Inventors: Stéphane Auffray, Saint Lyphard (FR); Hubert Voillaume, Issy les Moulineaux (FR)

(73) Assignee: AIRBUS, Blagnac (FR)

( * ) Notice: Subject to any disclaimer, the term of this patent is extended or adjusted under 35 U.S.C. 154(b) by 726 days.

(21) Appl. No.: 14/654,523

(22) PCT Filed: Dec. 20, 2013

(86) PCT No.: PCT/EP2013/077576
§ 371 (c)(1),
(2) Date: Jun. 20, 2015

(87) PCT Pub. No.: WO2014/096304
PCT Pub. Date: Jun. 26, 2014

(65) Prior Publication Data
US 2015/0346160 A1    Dec. 3, 2015

(30) Foreign Application Priority Data

Dec. 21, 2012  (FR) .................................. 12 62543

(51) Int. Cl.
*G01N 29/22* (2006.01)
*G01N 29/24* (2006.01)
(Continued)

(52) U.S. Cl.
CPC .......... *G01N 29/245* (2013.01); *B29C 70/44* (2013.01); *B29C 70/48* (2013.01); *B29C 70/54* (2013.01);
(Continued)

(58) Field of Classification Search
CPC ......... B29C 70/44; B29C 70/48; B29C 70/54; G01N 29/245; G01N 29/223
See application file for complete search history.

(56) References Cited

U.S. PATENT DOCUMENTS 4,701,659 A * 10/1987 Fujii .................... B06B 1/0688
                                                         310/334
6,370,964 B1     4/2002 Chang et al.
(Continued)

FOREIGN PATENT DOCUMENTS

| EP | 1 453 103 A2 | 9/2004 |
| FR | 2 821 012 A1 | 8/2002 |
| FR | 2 874 430 A1 | 2/2006 |

OTHER PUBLICATIONS

Kobayashi et al., "High-Temperature Piezoeletric Film Ultrasonic Transducers by a Sol-Gel Spray Technique and Their Application to Process Monitoring of Polymer Injection Molding," IEEE Sensors Journal, Feb. 1, 2006, pp. 55-61, vol. 6, No. 1, IEEE Service Center, New York, NY, US.
(Continued)

*Primary Examiner* — Joseph S Del Sole
*Assistant Examiner* — John Robitaille
(74) *Attorney, Agent, or Firm* — IM IP Law; C. Andrew Im; Chai Im (57) ABSTRACT

An ultrasound device for checking the quality of a composite material structure during the production cycle. Preferably, the device is incorporated into a production tooling performing the LRI process in which the composite material structure is placed between two molds during the production cycle. A layer of piezoelectric material is deposited on the face of one of the molds, opposite the face which is in contact with the structure. One face of an electrically insulating flexible material film is placed against the outer face of the piezoelectric material layer. The face of the film further includes conductive pads in contact with the piezoelectric material layer. Each pad is energized by electric voltage applied by a conductive strip. Each pad forms an independent ultrasonic transducer with the region of the piezoelectric material layer opposite of its placement.

12 Claims, 4 Drawing Sheets

(51) Int. Cl.
*B29C 70/48* (2006.01)
*B29C 70/54* (2006.01)
*B29C 70/44* (2006.01)

(52) U.S. Cl.
CPC ... *G01N 29/223* (2013.01); *G01N 2291/0231* (2013.01); *G01N 2291/0251* (2013.01); *G01N 2291/044* (2013.01); *G01N 2291/106* (2013.01)

(56) References Cited

U.S. PATENT DOCUMENTS

2005/0068041 A1    3/2005    Kress et al.
2008/0315462 A1    12/2008    Batzinger et al.
2011/0260581 A1    10/2011    Ghoshal et al.

OTHER PUBLICATIONS

Aggelis et al., "Monitoring of resin curing and hardening by ultrasound," Construction and Building Materials, Jun. 30, 2011, pp. 755-760, vol. 26, No. 1, Elsevier, NL.
Schmachtenberg et al., "Application of Ultrasonics for the process control of Resin Transfer Moulding," Polymer Testing, May 1, 2005, pp. 330-338, vol. 24, No. 3, Elsevier, Amsterdam, NL.

\* cited by examiner

Resin injection

Fig. 1

Resin injection

RECONFIGURABLE DEVICE FOR CHECKING A COMPOSITE STRUCTURE USING ULTRASOUND

RELATED APPLICATIONS

This application is a § 371 application from PCT/EP2013/077576 filed Dec. 20, 2013, which claims priority from French Patent Application No. 12 62543 filed Dec. 21, 2012, each of which is herein incorporated by reference in its entirety.

FIELD OF THE INVENTION

The invention relates to the general field of instrumentation means for monitoring the quality of production of structures made of composite material throughout the manufacturing process. It relates in particular to the means implementing sensors, transducers and ultrasounds to perform this monitoring.

BACKGROUND OF THE INVENTION

To inspect the production quality of structures made of composite material, during the very manufacturing process, it is known practice to use measurement means implementing ultrasound transducers whose function is to emit an ultrasound wave through the structure during production and pick up the wave that has passed through this structure, these transducers operating in a known manner by a transmission or reflection. The monitoring of manufacturing processes by ultrasound is thus generally performed by means of ultrasound sensors, of piezoelectric transducers, which support the baking temperatures applied during this process.

However, these means are generally incorporated in the manufacturing tools themselves so that the transducers used generally occupy positions that are fixed, predetermined, relative to the surface of the structure currently being manufactured. These sensors are arranged permanently on the tools and molds used for the production. They are generally glued onto the elements of these tools in contact with the structure currently being produced or, alternatively, inserted into these same elements which have then undergone a machining enabling them to incorporate these sensors.

Now, notably during the development phases of the methods for producing these structures made of composite material, in particular in the case of the manufacturing methods implementing the LRI (liquid resin injection) technique, the use of ultrasound instrumentation provides invaluable assistance. This assistance is nevertheless currently limited by the fact that ultrasound sensors are used whose position within the toolage cannot easily be modified, such a modification necessarily leading to a modification of the production means themselves.

However, it appears particularly advantageous to be able, if necessary, to more accurately observe one area of the structure to be produced rather than another, by increasing, for example, the number of measurement pathways in this area of interest and do so for the time necessary for this observation, and then be able to revert to a more standard sensor configuration, in which the sensors are, for example, distributed uniformly facing the structure currently being manufactured. For all that, such a possibility is truly advantageous only if the reconfiguration of the distribution of the sensors is neither lengthy to implement nor costly in terms of production equipment or processes, which is not the case with the ultrasound measurement devices currently used.

OBJECT AND SUMMARY OF THE INVENTION

One aim of the invention is to propose a solution to have a measurement means comprising a plurality of ultrasound sensors, intended to perform ultrasound measurements on parts made of composite material throughout the process of production of these parts, the ultrasound sensors being positioned at the level of the surface of the part being analyzed, this means making it possible to simply and inexpensively perform measurements with different sensor arrangements.

Another aim of the invention is to propose an ultrasound measurement means which, while cooperating with the means for manufacturing parts made of composite material that are to be inspected throughout the production process, is distinct from these means.

In other words, one aim of the invention consists in finding a solution to have an instrumentation that can easily be reconfigured and modified so as to optimize the ultrasound measurements which are themselves intended to optimize the production process.

To this end, the subject of the invention is a device for inspecting a structure made of composite material during its production, said structure being produced in a space limited by the inner face of a first form and by the inner face of a second form, said device comprising a plurality of ultrasound sensors arranged in the vicinity of the structure in such a way that each ultrasound sensor can emit an ultrasound wave into the structure and pick up the echo returned by this structure. The device comprises a layer of piezoelectric material whose inner face is arranged on the outer face of the second form and a film of electrically insulating flexible material arranged so as to be pressed against the outer face of the layer of piezoelectric material. Said film of flexible material comprises, on its face in contact with the layer of piezoelectric material, a plurality of electrodes, each electrode being able to be excited separately by a control signal transmitted via conductor. The conductive surface of each of the electrodes is arranged so as to be in contact with the surface of the layer of piezoelectric material such that each electrode forms, with the area of the layer of piezoelectric material facing which it is placed, a distinct ultrasound sensor.

According to various arrangements or properties, possibly used in conjunction, the device according to the invention can also present additional features.

Thus, according to one embodiment, the layer of piezoelectric material is directly formed on the outer face of the second form by the implementation of a sol-gel type method.

According to another embodiment, the electrically insulating film of flexible material is produced in a polymer material of polyimide type.

According to another embodiment, the electrodes are formed by conductive pads arranged on the surface, on the face of said film in contact with the layer of piezoelectric material, each electrode being electrically powered via a conductive element consisting of a conductive track arranged either on the opposite face of the film or in the thickness of the film.

According to a variant of the preceding embodiment, the conductive tracks powering the different electrodes are provided at their end with a connector system making it possible to apply an excitation voltage to each electrode.

According to another embodiment, each electrode consists of a single conductive pad whose dimensions are defined in such a way that the ultrasound sensor formed by this electrode and the layer of piezoelectric material emits a substantially planar ultrasound wave.

According to another embodiment, alternative to the preceding embodiment, each electrode consists of a conductive pad formed by a plurality of individual pads whose dimensions are defined in such a way that the ultrasound sensor formed by an individual pad and the layer of piezoelectric material emits a substantially spherical or cylindrical ultrasound wave; the individual pads being configured in such a way as to be able to be controlled separately.

According to a variant of the preceding embodiment, the individual pads are arranged relative to one another in such a way that they can be excited so as to constitute a single ultrasound sensor.

According to another embodiment, for each electrode, the excitation voltage is applied between said electrode and a common ground made up of the second form.

According to another embodiment, the layer of piezoelectric material deposited on the outer face of the second form has a thickness $e_2$ of the order of several tens of microns.

According to another embodiment, the film of flexible material has a thickness $e_1$ of the order of a few hundreds of microns.

Also a subject of the invention is a toolage for producing a structure made of composite material implementing the LRI method, said toolage comprising a first element, or mold, and a second element, or caul plate facing the first element, the structure produced being placed between the inner faces of these two elements. The toolage comprises an ultrasound inspection device according to the invention whose layer of piezoelectric material is formed on the outer face of the caul plate, the film of flexible material being, for its part, pressed against said layer.

DESCRIPTION OF THE FIGURES

The features and advantages of the invention will be better appreciated from the following description, the description being based on the attached figures which present.

DETAILED DESCRIPTION

For reasons of clarity, the device according to the invention is presented hereinbelow in the description through its application in the context of toolage for producing structures made of composite material implementing the LRI (liquid resin injection) method. This exemplary implementation is of course in no way limiting on the scope or the subject of the invention, the device according to the invention being able to be implemented and incorporated in any type of toolage for producing structures made of composite material, provided that these toolages comprise the elements with which the device according to the invention cooperates.

Figure 1:
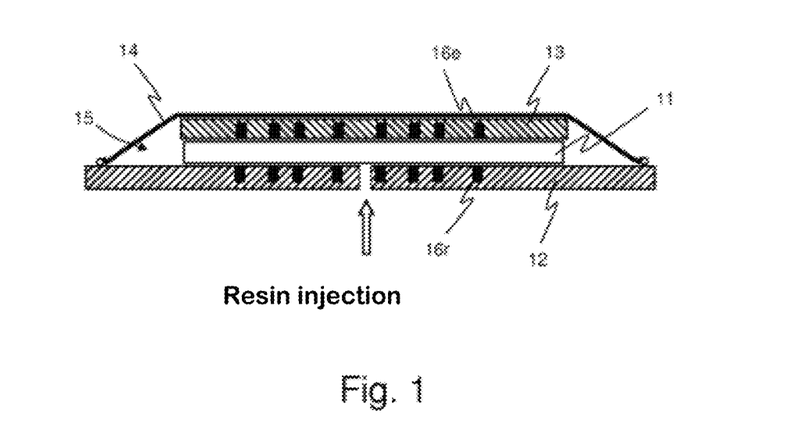
FIG. 1, a schematic illustration of a device for inspecting by ultrasound the production of a composite structure according to the prior art, in the context of a production by LRI method.

FIG. 1 very schematically presents a device for inspecting by ultrasound the production of a composite structure according to the prior art, in the context of toolage for producing structures made of composite material implementing the LRI method.

As is known, this production toolage comprises, in particular, an element 12, called mold, into which is injected the resin forming the structure made of composite material 11 to be produced and an element 13 called caul plate or "cover plate", which ensures the gauging in terms of thickness and flatness of the structure 11 to be injected, arranged in such a way that the structure currently being produced is placed between the mold 12 and the caul plate 13.

This toolage also comprises at least one membrane 14, a flexible wall, arranged in such a way as to delimit, with the mold 12, a space 15 surrounding both the structure 11 and the caul plate 13. This membrane 14 is moreover configured in such a way that it is possible to produce a vacuum in the space 15 such that, with the membrane gripping the caul plate 13 and the structure 11, the latter are pressed against one another and against the mold 12.

The ultrasound inspection device incorporated in this production toolage consists of a certain number of ultrasound sensors 16 arranged on the caul plate, the active surface of the sensors 16 being placed on the surface of the caul plate, facing the surface of the structure 11, so as to be able to propagate an ultrasound wave through the latter.

The number and the arrangement of the sensors 16 depend on the dimensions of the structure 11 produced and on the distribution of the areas of the structure 11 that are to be analyzed. Thus, if there is a desire, for example, to uniformly analyze the structure 11 produced, the ultrasound sensors 16 are arranged regularly facing the surface of the structure 11.

In order to ensure a correct positioning and orientation of the sensors 16 with respect to the structure 11 to be produced, and do so throughout the cycle of production of this structure, the sensors 16 are generally incorporated directly in the caul plate 13, as illustrated by FIG. 1. This type of mounting in effect makes it possible, because of the fact that the sensors 16 are driven into the caul plate 13, to ensure a correct positioning of the active faces of the sensors 16 with respect to the surface of the structure 11 currently being produced, and simplify the holding of these sensors in place.

Depending on the type of ultrasound analysis performed, analysis by transmission or analysis by reflection, the ultrasound sensors 16 used can each consist of a single element configured to emit or receive an ultrasound wave or else an emitting element 16e and a receiving element 16r. In the first case, the sensors 16 are located in only the caul plate 13, whereas, in the second case, illustrated by FIG. 1, the emitting element 16e is located in the caul plate 13 and the receiving element 16r is located in the mold 12, the active face of the receiving elements 16r then being directed toward the surface of the structure 11.

As has been stated previously, such a layout of the sensors in the production toolage offers the main advantage of making the placement of these sensors simple and permanent. Thus, if the aim is to produce a series of identical structures 11, there is no need to deposit the sensors 16 to extract a structure at the end of production just as there is no need to proceed with a new mounting of the sensors to launch the production of the next structure.

On the other hand, such a layout presents the major inconvenience of creating a particular caul plate 13 and possibly mold 12, the mold and the caul plate then being suited to a particular test and a fixed arrangement, particular distribution, of the sensors 16 facing the surface of the structure 11 to be inspected.

Consequently, if, for various reasons, there is a desire to proceed with a different arrangement of the sensors 16, it becomes necessary to modify the caul plate 13 and possibly the mold 12, which constitutes a costly operation and entails devoting time to the dismantling and the reassembly of these elements, which is prejudicial in terms of production rate.

Figure 2:
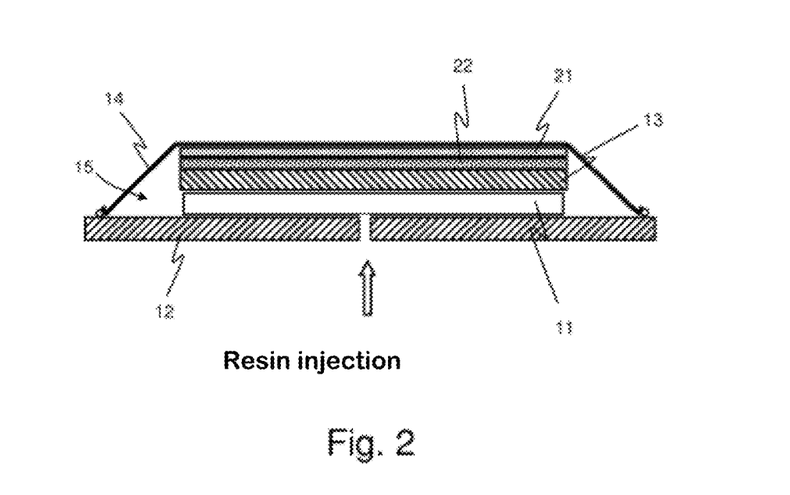
FIG. 2, a schematic illustration of a device for inspecting by ultrasound the production of a composite structure according to the invention, in the context of a production by LRI method.

FIG. 2 presents a general schematic view of the ultrasound inspection device according to the invention, shown in an equipment configuration similar to that of the device of FIG. 1, known from the prior art. The configuration presented here, which corresponds to a reflection analysis, can easily be adapted to a transmission analysis.

As illustrated by FIG. 2, the device according to the invention comprises two distinct elements which cooperate, a layer of piezoelectric ceramic 22 and a film of flexible material 21.

The layer of piezoelectric ceramic 22 is a thin layer arranged on the outer face of the caul plate 13, that is to say the face opposite the face in contact with the surface of the structure 11, which covers all of the caul plate, or at least all of the surface of the caul plate situated facing the structure 11 to be inspected.

According to a preferred embodiment of the invention, the layer 22 of piezoelectric ceramic is produced by a sol-gel type method, from a substrate deposited in liquid or viscous phase on the outer surface of the caul plate, by "piezospray" technique for example, and hardened.

However, any method known to those skilled in the art making it possible to deposit a thin layer of piezoelectric material on the surface of the caul plate can alternatively be used to produce the layer 22.

The film 21 of flexible material is, for its part, configured in such a way as to be pressed against the outer surface of the layer 22 of piezoelectric ceramic, that is to say the face opposite the face in contact with the surface of the caul plate 13.

Figure 3:
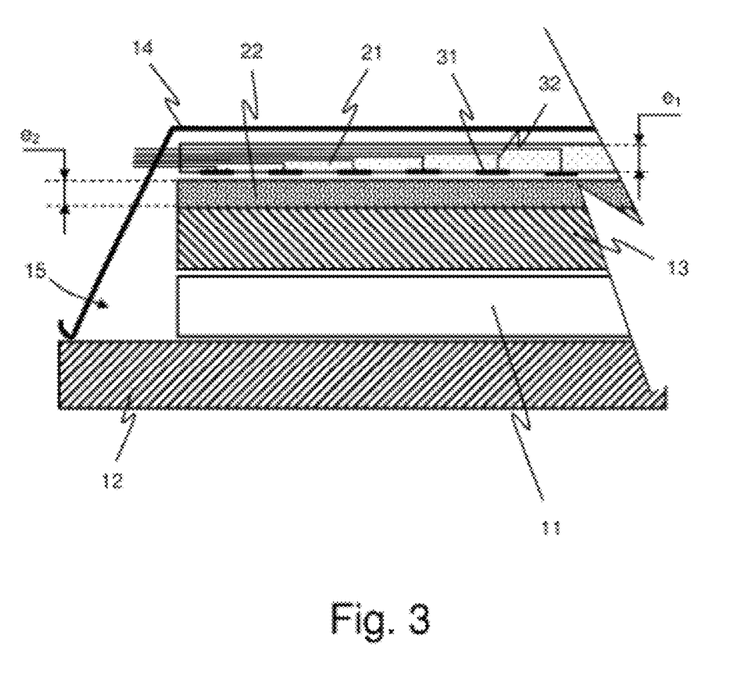
FIG. 3, a partial schematic view of toolage for producing a structure by LRI method incorporating the device according to the invention.

According to the invention, as illustrated by the detailed view of FIG. 3, this film 21 comprises a plurality of electrodes 31 of small thickness, arranged on the surface. The face 33 of said film 21 which bears the electrodes 31 is intended to be pressed against the outer face of the layer 22 of piezoelectric material. The film 21 also comprises a set of electrical conductors 32, which emerge from the film through an appropriate connector system and which make it possible to apply an electrical signal to each of the electrodes 31.

Also according to the invention, the film 21 can be produced in any appropriate flexible electrically insulating material, notably exhibiting the requisite temperature and pressure withstand characteristics, the temperature and pressure conditions being those imposed by the method for producing the structure 11. Preferentially, the film 21 is a film of polymer material from the group of polyimides, for example a film of Kapton®.

With respect to the electrodes 31 and the conductors 32, these are preferentially produced, in the manner of a printed circuit, in the form of pads and tracks of conductive material, metal pads and tracks for example.

As illustrated by FIG. 3, the pads forming the electrodes 31 are deposited on the surface, on those of the faces of the flexible film 21 intended to be placed in contact with the layer 22 of piezoelectric material. The conductive tracks 32, for their part, are located on the other face or else, as illustrated by FIG. 3, in the thickness of the film, so as not to come into contact with the layer of piezoelectric material 22.

The set of conductive electrodes-tracks is moreover produced and incorporated in the flexible film by any appropriate flexible printed circuit production method known to those skilled in the art.

From a dimensional point of view, the layer 22 of piezoelectric material deposited on the caul plate has a thickness $e_2$ of the order of a few tens of microns, typically of the order of 70 μm, whereas the film 21 of flexible material has a thickness $e_1$ of the order of a few hundreds of microns, typically of the order of 200 μm. The electrodes 31 and the conductive tracks 32 located on the film 21, for their part, have a thickness of the order of 10 or so microns to a few tens of microns. It should moreover be noted that the thickness and the nature of the film of piezoelectric material determines the resonance frequency of the layer 22.

From a functional point of view, the assembly consisting of the layer of piezoelectric material deposited on the caul plate and the electrodes 31 arranged on the surface of the film of flexible material 21 form a plurality of ultrasound sensors arranged on the surface of the caul plate facing the structure 11 to be analyzed, the distribution of the ultrasound sensors formed in this way being simply defined by the arrangement of the electrodes on the surface of the flexible film.

When it is excited by an electrical signal, voltage, each of the electrodes forms, with the area of the layer of piezoelectric material situated between it and the surface of the caul plate, a piezoelectric transducer capable of emitting an ultrasound wave through the structure 11 and of picking up the echo produced by the passage of this signal through the structure 11. Thus, there is advantageously produced a set of ultrasound sensors whose operation is identical, in principle, to that of the individual sensors 16 presented in FIG. 1.

It should be noted that, to ensure a good operation of the duly produced ultrasound sensors, it is necessary to ensure the best possible contact between the electrodes 31 on the one hand and the surface of the layer 22 of piezoelectric material on the other hand. This contact is assured by pressing the face of this flexible film which bears these electrodes onto the surface of the layer 22 by any appropriate means, suited to the operation of the production toolage in which the ultrasound inspection device according to the invention is incorporated. In the context of a production toolage implementing a method of LRI type, such as that schematically represented in FIGS. 2 and 3, the contact between the film 21 and the piezoelectric layer 22 can advantageously be maintained, incidentally, by the partial vacuum introduced into the space 15 delimited by the membrane 14 which encloses the structure 11 during production, and the caul plate 13 on which the layer of piezoelectric material 22 is deposited and the flexible film 21 on which the electrodes 31 are arranged.

The structure described in the text above advantageously makes it possible to produce a device comprising a plurality of ultrasound sensors, acoustic transducers, having functionalities similar to that of the ultrasound sensors generally used, while offering a greater ease of placement and of use.

In effect, in the known devices generally used, the sensors are incorporated in the very structure of the caul plate 13 and possibly of the mold 12. Consequently, modifying the number and the distribution of the sensors on the surface of the part to be inspected entails modifying or replacing the caul plate 13 and possibly the mold 12 so as to house therein the sensors according to the desired new arrangement.

Now, in the case of the device according to the invention, insofar as the layer of piezoelectric material deposited on the surface of the caul plate is a uniform layer and one in which the arrangement of the sensors is defined simply by the arrangement of the conductive pads forming the electrodes 31 on the surface of the flexible film 21, changing the arrangement and the number of the sensors becomes advantageously simple and requires only the replacement of the flexible film 21. An inspection device is thus available which can easily be reconfigured by simple replacement or repositioning of the flexible film 21, the replacement of the existing flexible film with another film having a different arrangement of electrodes advantageously having a cost lower than the costs generated by the modification or the replacement of the caul plate 13 and possibly of the mold 12.

FIGS. 4 to 7 reveal another advantage offered by the use of the device according to the invention, an advantage stemming from the variety of sensor configurations that can be implemented because of the very structure of the device according to the invention.

As has been stated previously, each sensor of the device according to the invention consists of the corresponding electrode arranged on the flexible film 21 and of the area of the layer 22 of piezoelectric material situated facing this electrode. This way, the characteristics of each of the sensors of the device according to the invention can be defined separately by simply acting on the form of the electrodes 31 arranged on the flexible film 21, each electrode being able to have its own form and dimensions.

Figure 4:
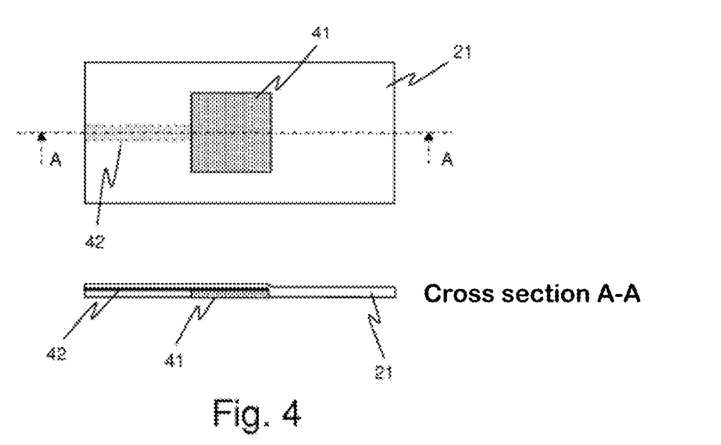
FIG. 4, a schematic illustration of an embodiment of the device according to the invention.

FIG. 4 shows a flat general view of a first type of electrode that can be implemented by the device according to the invention.

In the case of FIG. 4, it is an electrode consisting of a single conductive pad 41 whose dimensions, length and width or even diameter depending on the form of electrode, are defined in such a way as to emit, into the structure 11 being analyzed, a substantially planar wave that has, for the emitted acoustic frequency, sufficient power to pass through the structure, while retaining a sufficient analysis resolution. Thus, for an acoustic frequency of 5 MHz, a frequency determined by the characteristics of the piezoelectric coating, pads in the form of squares of 5 mm side will for example be chosen.

Such a pad is excited by the application of an appropriate voltage via a conductive track 42 linked externally to a voltage generator, a track which runs for example in the thickness of the film 21.

Figure 5:
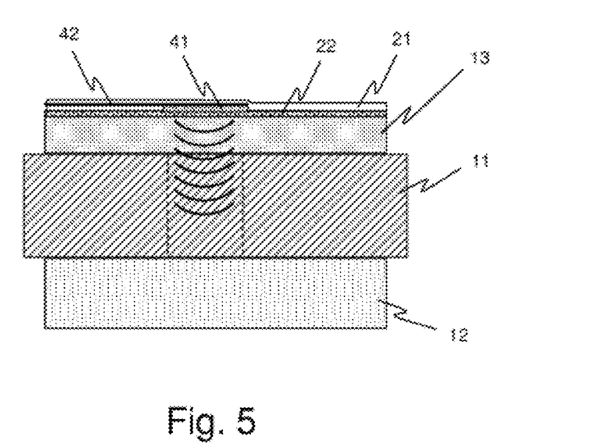
FIG. 5, an illustration of the principle of operation of the device in the embodiment of FIG. 4.

Equipped with such pads, the device according to the invention then behaves, as illustrated by FIG. 5, in a manner similar to the known ultrasound inspection devices comprising unitary sensors incorporated in the production toolage, but one that retains its advantageous characteristics in terms of placement and interchangeability.

Figure 6:
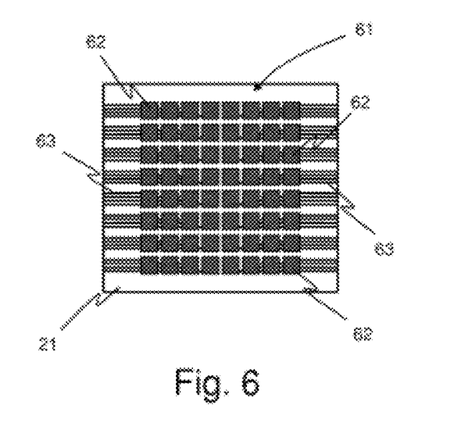
FIG. 6, a schematic illustration of another embodiment of the device according to the invention.

FIG. 6 presents a general view of a second type of electrode 61 that can be implemented by the device according to the invention in a more sophisticated embodiment. The electrode presented in FIG. 6 consists of a plurality of individual electrodes 62 grouped together to form a set exhibiting a particular arrangement, a matrix arrangement for example in the case of FIG. 6.

In this exemplary implementation, each of the individual electrodes 62 is configured in such a way as to be able to be excited independently by the application of an appropriate voltage via a conductive track 63 linked externally to a voltage generator.

The dimensions and the form of the individual electrodes 62 are defined in such a way that each individual electrode produces, when it is excited, a substantially spherical or cylindrical wave. This way, depending on the voltage applied to each of the individual electrodes and the respective instants of excitation of the different electrodes, it is possible to emit a soundwave exhibiting particular characteristics. Each electrode 61 of the device then makes it possible to form, in an advantageously simple manner, a multi-element ultrasound sensor whose acoustic characteristics in terms of accuracy and resolution can be substantially different from those of a traditional acoustic sensor such as those with which the known test devices are equipped.

Figure 7:
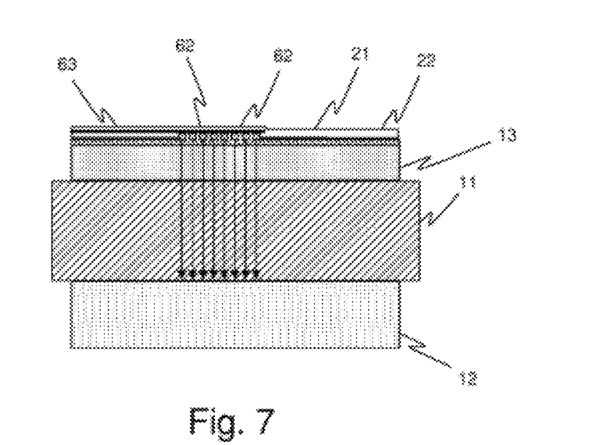
FIG. 7, an illustration of the principle of operation of the device in the embodiment of FIG. 6.

The illustration of FIG. 7 presents, by way of example, a particular application for which the individual electrodes 62 forming one and the same electrode 61 are excited in such a way as to each emit an individual acoustic wave that is propagated through the structure 11.

The invention claimed is:

1. An ultrasonic control device to inspect a structure made of composite material during its production, the structure being produced in a space limited by an inner face of a first form and by an inner face of a second form, the device comprising:
   a plurality of ultrasound sensors arranged in a vicinity of the structure, each ultrasound sensor emits an ultrasound wave into the structure and picks up an echo returned by the structure;
   a layer of piezoelectric material, an inner face of the piezoelectric material is placed on an outer face of the second form; and
   a replaceable film of electrically insulating flexible material arranged to be pressed against an outer face of the layer of piezoelectric material, the replaceable film of electrically insulating flexible material comprises, on a face in contact with the layer of piezoelectric material, a plurality of electrodes, each electrode is configured to be excited separately by a control signal transmitted via a conductor;
   a conductive surface of said each electrode is arranged to be in contact with the outer face of the layer of piezoelectric material such that said each electrode forms, with an area of the layer of piezoelectric material facing which said each electrode is placed, a distinct ultrasound sensor;
   wherein an arrangement of the plurality of ultrasound sensors is modifiable by altering the arrangement of the plurality of the electrodes; and
   wherein the ultrasonic control device is reconfigurable by replacing or repositioning the replaceable film on the outer face of the layer of piezoelectric material to alter the arrangement of the plurality of electrodes.

2. The device as claimed in claim 1, wherein the layer of piezoelectric material is produced by a sol-gel type method and is directly formed on the outer face of the second form.

3. The device as claimed in claim 1, wherein the film of electrically insulating flexible material is a polymer material of polyimide type.

4. The device as claimed in claim 1, wherein the plurality of electrodes comprise conductive pads arranged on a surface of the face of the film in contact with the layer of piezoelectric material, said each electrode is electrically powered via a conductive element comprising a conductive track arranged either on an opposite face of the film or within the film.

5. The device as claimed in claim 4, wherein the conductive tracks powering different electrodes comprise, at their respective end, a connector system to apply an excitation voltage to said each electrode.

6. The device as claimed in claim 1, wherein said each electrode comprises a single conductive pad whose dimensions are defined such that the ultrasound sensor formed by said each electrode and the layer of piezoelectric material emits a substantially planar ultrasound wave.

7. The device as claimed in claim 1, wherein said each electrode comprises a conductive pad formed by a plurality of individual pads whose dimensions are defined such that the ultrasound sensor formed by an individual pad and the layer of piezoelectric material emits a substantially spherical or cylindrical ultrasound wave; the plurality of individual pads is configured to be controlled separately.

8. The device as claimed in claim 7, wherein the plurality of individual pads is arranged relative to each other such that the plurality of individual pads can be excited to constitute a single ultrasound sensor.

9. The device as claimed in claim 1, wherein the second form constitutes a common ground; and wherein said each electrode is configured to be excited by an excitation voltage applied between said each electrode and the common ground.

10. The device as claimed in claim 1, wherein the layer of piezoelectric material deposited on the outer face of the second form has a thickness in an order of several tens of microns.

11. The device as claimed in claim 1, wherein the film of electrically insulating flexible material has a thickness in an order of a few hundreds of microns.

12. Toolage for producing a structure made of composite material by a liquid resin injection method, the toolage comprising:
 a first element or mold;
 a second element or caul plate facing the first element, the structure to be produced is placed between inner faces of the first and second elements; and
 a device for inspecting the structure made of composite material as claimed in claim 1, the layer of piezoelectric material being formed on an outer face of the caul plate, the film of electrically insulating flexible material being pressed against the layer of piezoelectric material.

* * * * *